US005632984A

United States Patent [19]
Wong et al.

[11] Patent Number: 5,632,984
[45] Date of Patent: May 27, 1997

[54] METHOD OF TREATMENT OF MACULAR DEGENERATION

[75] Inventors: Vernon G. Wong, Rockville, Md.; King Y. Lee, Mission, Kans.; Jerry B. Gin, Sunnyvale, Calif.

[73] Assignee: Oculex Pharmaceuticals, Inc., Sunnyvale, Calif.

[21] Appl. No.: 314,534

[22] Filed: Sep. 28, 1994

Related U.S. Application Data

[63] Continuation of Ser. No. 95,735, Jul. 22, 1993, abandoned.
[51] Int. Cl.$^6$ .................................................. A61K 38/21
[52] U.S. Cl. ...................... 424/85.4; 424/85.7; 424/427
[58] Field of Search ............................... 424/85.4, 85.7, 424/427

[56] References Cited

U.S. PATENT DOCUMENTS 4,853,224  8/1989  Wong .

OTHER PUBLICATIONS

Baron et al., "The Interferons: Mechanism of Action and Clinical Applications", *J. of the Am. Medical Assoc.*, 266:1375 (1991).
Brouty–Boy´ and Zetter, "Inhibition of Cell Motility by Interferon", *Science*, 208:516–518 (1980).
Celtrix News Release, "Celtrix Acquires Baltimore Biotech and Announces Human Studies to Treat Macular Degeneration", Sep. 14, 1992.
Dayton, "Treatment for Blindness Challenges Eye Orthodoxy", *New Scientist*, Mar. 21 Issue, p. 21 (1992).
Engler et al., "Interferon Alpha–2a Treatment of Patients with Subfoveal Neovascular Macular Degeneration", *Acta Ophthalmologica*, 71:27–31 (1993).
Folkman and Klagsbrun, "Angiogenic Factors", *Science*, 235:442–447 (1987).
Fung, "Interferon Alpha 2a for Treatment of Age–Related Macular Degeneration", *Am. J. of Ophthalmology*, 112(3):349–350 (1991).
Glazer et al., "Transforming Growth Factor–$\beta_2$ for the Treatment of Full–thickness Macular Holes", *Ophthalmology*, 99(7):1162–1173 (1992).
Guyer et al., "Interferon–Associated Retinopathy", *Arch Ophthalmology*, 111:350–356 (1993).
Guyer et al., "Systemic Antiangiogenic Therapy for Choroidal Neovascularization", *Arch Ophthalmology*, 110:1383–1384 (1992).
Heller, "Biodegradable Polymers in Controlled Drug Delivery", *CRC Critical Reviews in Therapeutic Drug Carrier Systems*, vol. 1, CRC Press, Boca Raton, FL, pp. 39–90 (1987).
Heller, "Bioerodible Hydrogels", *Hydrogels in Medicine and Pharmacy*, vol. III, N.A. Peppes ed., CRC Press, Boca Raton, FL, pp. 137–149 (1987).

Karaçorlu, MD, "Lack of Toxicity of Intravitreally Administered Interferon Alpha–2a", *Ophthalmic Surgery*, 23(12):833–835 (1992).
Loughnan et al., "Treatment of Subfoveal Choroidal Neovascular Membranes with Systemic Interferon–α2a", *Aust. and New Zea. J. of Ophthalmol.*, 20(3):173–175 (1992).
Penn et al., "The Mystery of Pre–Retinal Neovascularization in the Rat Model of Retinopathy of Prematurity", Association for Research in Vision and Ophthalmology, Annual Meeting Abstracts , Paper #2937 published in *Invest. Ophthalmol. & Visual Science*, vol. 33 (1992).
Reynaud et al., "Intermittent Hypoxia Stimulates Neovascularization in the Rat Model of Retinopathy of Prematurity", Association for Research in Vision and Ophthalmology, Annual Meeting Abstracts, Paper #2940 published in *Invest. Ophthalmol. & Visual Science*, vol. 33 (1992).
Sabbagh, "Know When Interferon Treatment Can Succeed for ARMD: Prognosis is Best for Immature and Most Choroidal Neovascular Membranes", *Ophthalmology Times*, Mar. 1 Issue, p. 6 (1993).
Thomas and Ibanez, "Interferon Alfa–2a in the Treatment of Subfoveal Choroidal Neovascularization", *Am. J. of Ophthalmol.*, 115:563–568 (1993).
White et al., "Treatment of Childhood Angiomatous Diseases with Recombinant Interferon Alfa–2a", *The J. of Pediatrics*, 118(1):59–66 (1991).
White et al., "Treatment of Pulmonary Hemangiomatosis with Recombinant Interferon Alpha–2a", *N.E. Journal of Medicine*, 320:1197 (1989).
Williams et al., "Effect of Plasminogen Activator Inhibitor Type 2 (PAI–2) on Neovascularization", Association for Research in Vision and Ophthalmology, Annual Meeting Abstracts, Paper #1942 published in *Invest. Ophthalmol. & Visual Science*, vol. 33 (1992).
Bioworld, "Growth Factor slows Retinal Degeneration", vol. 2, #195, 1990.
Poliner et al Ophthalmology (1993) vol. 100, 1417–1424.
Gillies et al Br. J. Ophthalmol (1993) 77, pp. 759–765.
Guyer et al Arch Ophthalmol (1992) 110, pp. 1383–1384.
Smith et al., Cornea, 8(1), pp. 58–61, 1989.
Vegh et al., Ophthalmic Surg., 17(2) pp. 103–105, 1986.
Dharma et al., Ophthalmic Surg., 18(1), pp. 51–54, 1987.

*Primary Examiner*—Chhaya D. Sayala
*Attorney, Agent, or Firm*—Bertram I. Rowland; Flehr, Hohbach, Test, Albritton & Herbert

[57] ABSTRACT

Intraocular administration of drugs such as α-2a interferon is employed in the treatment of age-related macular degeneration. Intraocular administration obviates the side effects associated with systemic administration, concentrates the drug at the site of the disease, and, where microcapsules are employed, provides continuous, long-lasting treatment.

9 Claims, No Drawings

METHOD OF TREATMENT OF MACULAR DEGENERATION

This application is a continuation of Ser. No. 08/095,735 filed Jul. 22, 1993, now abandon.

TECHNICAL FIELD

Methods and compositions are provided for the treatment of macular degenerative diseases.

BACKGROUND

Age-related macular degeneration (AMD) is the leading cause of irreversible central vision loss (20/200 or worse) among people in the United States aged 52 or older. AMD is the most common overall cause of blindness in the United States, Canada, Britain, and Australia. AMD is a degenerative disease of the macula, the area of the retina that is responsible for central vision and color perception. AMD tends to become worse with time and can best be described as a process of "wear and tear." Thus, the prevalence of severe visual loss increases with age. AMD encompasses several types of abnormalities that develop in the macula of older people. These abnormalities range from mild, with no loss of vision, to severe, with loss of all straight-ahead vision. Because the peripheral retina is unaffected by AMD, side vision is retained along with the ability to see in the dark. Most affected is the ability to see fine detail, to read, and to see well enough in the distance to drive.

The macula is the portion of the retina which lies directly behind the lens. The cones, light-sensitive cells which are responsible for central vision, are heavily concentrated in the macula. The peripheral retina is composed mainly of rods, the light-sensitive cells responsible for side and night vision. The macula is one hundred times more sensitive to detail than the peripheral retina. In a healthy macula, the clear layer of the retina on the inside of the eye is nourished and maintained by an adjoining layer called the pigment epithelium. Behind the pigment epithelium is the choroid which contains the blood vessels that transport nourishment to and carry waste material away from the retina.

There are three major forms of macular degeneration: dry (also known as atrophic), wet (also known as disciform, exudative, or neovascular), and pigment epithelial detachment. The dry form, which occurs in more than 85% of AMD patients, leads to gradual vision loss and can be a precursor to the wet form. The dry form results from an inability of the pigment epithelium to digest the cone tips that the retina produces as waste materials. The pigment epithelium may swell and die as a result of the collection of undigested waste materials. An early warning sign of dry macular degeneration is the formation of yellow spots, termed drusen, on the retina which result from the collection of undigested waste materials.

The wet form of macular degeneration, which occurs in about 10% of AMD patients, is associated with a sudden vision loss, resulting from the growth of new, abnormal blood vessels, also termed subretinal (choroidal) neovascularization (SRNV), under the pigment epithelium of the retina. The fluid and blood that leak from these new blood vessels cause the macula to bulge, resulting in distorted vision. As the disease progresses the cones are flooded and separated from their source of nourishment. Without nourishment, the cones degenerate and die, causing permanent blind spots. Pigment epithelial detachment, the third form of macular degeneration, may result with continued SRNV beneath the pigment epithelium, forcing it to detach from the choroid. Pigment epithelial detachment occurs in less than 5% of AMD patients.

Drusen, although used as an indicator of the development of macular degeneration, are currently not treated. Instead, patients with drusen are closely monitored through regular eye exams. At present there is no therapeutic or surgical treatment for the dry form of AMD. However, the dry form of AMD is accompanied by only gradual vision loss and the concomitant damage is usually not as severe, nor as sudden as, the damage associated with the wet form of AMD. Eyesight in patients with the dry form of AMD may be helped by special low vision spectacles or by learning to use side vision to accommodate for the loss of central vision. Because the dry form can lead to the wet form, patients are encouraged to monitor their vision using the Amsler Grid. This simple test can detect early retinal deformation caused by neovascularization associated with the wet form of macular degeneration.

At present there is no cure for AMD. The only treatment available for SRNV associated with the wet form of macular degeneration is laser photocoagulation. A narrow, highly focused beam of laser light is directed at the abnormal blood vessels. The heat produced by the laser dries up leaking blood vessels and inhibits further leakage, bleeding, and growth. However, laser treatment is effective only in selected classic cases, which include only about 25% of wet form patients (Bressler, N. M. (1990) *Recent Advances in Management of Occult Age-Related Macular Degeneration*, RPB Science Writers Seminar in Ophthalmology, Universal City, Calif.). Furthermore, patients treated with laser photocoagulation suffer a rapid and high rate of recurrence (10% within two months, 53% within three years following treatment). Laser treatment is also quite destructive and may result in irreversible damage to the retina. No therapeutic treatments are available for treating AMD, although current research has identified several drug candidates including: growth hormones, such as basic fibroblast growth factor (bFGF) and transforming growth factor β(TGF-β); neurotrophic factors, such as brain-derived neurotrophic factor (BDNF); regulators of neovascularization, such as plasminogen activator factor type 2 (PAI-2); anti-inflammatory drugs, such as dexamethasone; antioxidants; and forms of interferon, such as α-2a interferon.

All of the proposed therapies employ systemic injection of the drug candidate. However, preliminary studies using systemic injection of α-2a interferon have proven to be equivocal and in some cases deleterious due to marked side effects [Thomas and Ibanez (1993) *Am J Ophthalmol* 115(5): 563–8, Engler, et at. (1993) *Acta Ophthalmol* 71(1): 27–31, Loughnan, et at. (1991) *Am J Ophthalmol* 20(3): 173–5]. Clearly there is a need for a successful therapy for AMD. The subject invention provides such a therapy, providing for efficacious administration of the drug of choice by intraocular inoculation. The subject invention also provides a method whereby controlled intraocular release of the drug of choice is achieved over extended periods of time.

Relevant Literature

Current therapies and advances are reviewed in Bressler, N. M. (1990) *Recent Advances in Management of Occult Age-Related Macular Degeneration*, RPB Science Writers Seminar in Ophthalmology, Universal City, Calif.

Use of α-2a interferon in the treatment of childhood angiomatous disease is described in White, et al. (1991) *J Pediatr* 118: 59. The in vitro activities of α-2a interferon as inhibitors of endothelial cell migration and as protectors of endothelial cell growth factor receptors from activation by their ligands are described in Brouty-Boye and Zetter (1980) *Science* 208: 516 and Folkman and Klagsbrun (1987) *Science* 235: 442, respectively.

The efficacy of systemic injection of α-2a interferon for treatment of macular degeneration in humans is described in Fung, W. E. (1991) *Am J Ophthalmol* 112: 349, Fung, W. E. (1991) *Am Acad Ophthalmol, Annual Meeting Abstracts*, page 123, poster no. 214, and Sabbagh, L. B. (1993) *Ophthalmology Times* March 1 issue, page 6.

Thomas and Ibanez (1993) *Am J Ophthalmol* 115(5): 563-8, Engler, et at. (1993) *Acta Ophthalmol* 71(1): 27-31, Loughnan, et at. (1992) *Australia and New Zealand Am J Ophthalmol* 20(3): 173-5, Guyer, et at. (1992) *Arch Ophthalmol* 110: 1383-1384 describe equivocal and deleterious results with the use of systemic injection of α-2a interferon in the treatment of macular degeneration. Guyer, et at. (1993) *Arch Ophthalmol* 111: 350-356 describe retinopathy associated with systemic injection of interferon.

Intravitreal injection of interferon in rabbits and the lack of toxicity associated with such treatments is described by Karacorlu, et al. (1993) *Ophthalmic Surg* 23: 833-835.

A method for treatment of diseases of the eye using microcapsules (biodegradable ocular implants), as well as a method for preparation of microcapsules, is disclosed in U.S. Pat. No. 4,853,224. Encapsulation for controlled drug delivery is described in Heller (1), Biodegradable Polymers in Controlled Drug Delivery, In: CRC Critical Reviews in Therapeutic Drug Carrier Systems, Vol. 1, CRC press, Boca Raton, Fla., 1987, pp. 39-90. Bioerodible polymers are described in Heller (2), In: Hydrogels in Medicine and Pharmacy, Vol. III, N. A. Peppes ed., CRC Press, Boca Raton Fla., 1987, pp. 137-149.

Use of TGF-β in treatment of macular degeneration is described in Glaser, et at. (1992) *Ophthalmology* 99: 1162 and in a Press Release from Celtrix Pharmaceuticals, Inc., Sep. 14, 1992. Other references relating to the treatment of macular degeneration include: Williams, et al. (1992) *Association for Research in Vision and Ophthalmology, Annual Meeting Abstracts*, Paper #1942 published in *Invest Ophthalmol Visual Science* Vol. 33; Penn, et al. (1992) *Association for Research in Vision and Ophthalmology, Annual Meeting Abstracts*, Paper #2937 published in *Invest Ophthalmol Visual Science* Vol. 33; Reynaud, et al. (1992) *Association for Research in Vision and Ophthalmology, Annual Meeting Abstracts*, Paper #2940 published in *Invest Ophthalmol Visual Science* Vol. 33; Dayton (1992) *New Scientist* (1992) March 21 Issue, p. 21; and (Oct. 9, 1990) *BioWorld* Vol. 2, No. 195.

SUMMARY OF THE INVENTION

Methods and compositions are provided for the effective treatment of macular degeneration by the administration of drugs into the posterior segment of the eye to provide a therapeutically effective amount of the drug to inhibit subretinal neovascularization. Of particular interest is the administration of interferon, particularly α-2a interferon. In one embodiment of the invention biocompatible, biodegradable microcapsules containing the drug of choice are employed to provide for slow release of the drug and maintenance of a therapeutically effective drug concentration for an extended period of time.

DESCRIPTION OF THE SPECIFIC EMBODIMENTS

Macular degeneration is treated by the intraocular introduction of a drug shown to be effective in the inhibition of subretinal neovascularization. Introduction of the drug into the posterior segment allows diffusion of the drug throughout the vitreous within the posterior segment (or in the case of patients who have undergone vitrectomy, the cavity or space occupying the posterior segment) and further into the entire retina, the choroid and the opposed sclera. Thus, the drug will be directly available at the macula, the site where the drag is needed, and will he maintained at an effective dosage.

The wet form of macular degeneration and pigment epithelial detachment are forms of AMD which are amenable to treatment using the method of the subject invention. In both of these forms of macular degeneration, the disease is associated with SRNV. Neovascularization may be inhibited by administration of interferon to the site of blood vessel growth, thus promoting a decrease in leakage and hemorrhage from the subretinal neovascular membrane (SRNM) and the eventual obliteration of the abnormal vessels.

The drugs of choice in the method of the subject invention include any of the various interferons, including the α-, β-, or γ-interferons, particularly the α-interferons, more particularly α-2a interferon. The interferons may be modified from natural interferon, i.e. chimeric, fused interferons produced through combination with, for example, other interferons using techniques known in the art such as protein fusion, chemical cross-linking, or the like; fragments of interferons which retain the activity of the native protein; or small organic molecules with interferon-like activity. The choice of interferon for administration will be influenced by its solubility within the vitreous humor or within the fluid occupying the posterior segment of the vitrectomized eye. α-2a interferon is sufficiently soluble in the vitreous to be presented at a pharmacologically effective dose within the posterior segment of the eye. Other interferons, such as α-2a interferon, which may find use in the method of the subject invention are commercially available or may be produced in accordance with methods described in the art.

The method of treatment of the subject invention may also employ the use of microcapsules. Microcapsules provide another mode of delivery of interferon to the posterior segment of the eye. Intraocular inoculation of microcapsules containing interferon achieves concentration of the drug at the site and retention of the drug within the posterior segment of the eye. The method of preparation of microcapsules containing drugs such as α-2a interferon and a method of use of these microcapsules is disclosed in U.S. Pat. No. 4,853,224, herein incorporated by reference.

The composition of the microcapsule will consist of a biodegradable polymer. For the most part, the polymeric compositions will be organic esters or ethers, which when degraded result in physiologically acceptable degradation products, including the monomers. However, anhydrides, amides, orthoesters or the like, by themselves or in combination with other monomers may also find use. The polymers may be addition or condensation polymers, particularly condensation polymers. The polymers may be cross-linked or non-cross-linked, usually not more than lightly cross-linked, generally less than 5%, usually less than 1%. For the most part, besides carbon and hydrogen, the polymers will include oxygen and nitrogen, particularly oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller (1), Biodegradable Polymers in Controlled Drug Delivery, In: CRC Critical Reviews in Therapeutic Drug Carrier Systems, Vol. 1, CRC press, Boca Raton, Fla., 1987, pp. 39-90, herein incorporated by reference, may find use in the present invention.

Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate, a slowly eroding polymer is achieved, while erosion is substantially enhanced with the lactate raecemate.

Among the polysaccharides will be calcium alginate, and functionalized celluloses, particularly carboxymethylcellulose esters characterized by being water insoluble, having a molecular weight of about 5 kD to 500 kD, etc. Other polymers of interest include polyvinyl alcohol, esters and ethers, which are biocompatible and may be biodegradable. For the most part, characteristics of the polymers will include biocompatibility, compatibility with interferon, ease of encapsulation, a half-life in the physiological environment of at least 6 hrs, preferably greater than one day, low or no viscosity enhancement of the vitreous, water insolubility, and the like.

The biodegradable polymers which form the microencapsulated particles will desirably be subject to enzymatic or hydrolytic instability. Water soluble polymers may be cross-linked with hydrolyric or biodegradable unstable cross-links to provide useful water insoluble polymers. The degree of stability can be varied widely, depending upon the choice of monomer, whether a homopolymer or copolymer is employed, or whether mixtures of polymers are employed, where the polymers may be employed as varying layers or mixed.

By employing a biodegradable polymer in the microcapsule, particularly a polymer where the biodegradation is relatively slow, the rate of release of the drug will be primarily diffusion controlled, depending upon the surrounding membrane or monolithic polymer structure, rather than breakdown of the particle. For the most part, the selected particles will have lifetimes at least equal to the desired period of administration, preferably at least twice the desired period of administration, and may have lifetimes of 5 to 10 times the desired period of administration. The particles will thus have lifetimes so as to maintain an effective concentration of the drug in the posterior segment for a period of ranging from at least about 2 weeks to 14 months, more usually from at least about 3 months to 10 months, preferably about 4 months.

The particles may be substantially homogeneous as to composition and physical characteristics or heterogeneous. Thus, particles can be prepared where the center may be of one material and the surface have one or more layers of the same or different composition, where the layers may be cross-linked, or of different molecular weight, different density or porosity, or the like. For example, where it is desirable to quickly release an initial bolus of drug, the center may be a polylactate coated with a polylactate-polyglycolate copolymer, so as to enhance the rate of initial degradation. Most ratios of lactate to glycolate employed will be in the range of about 1:0.1. Alternatively, the center may be polyvinyl alcohol coated with polylactate, so that on degradation of the polylactate the center would dissolve and be rapidly washed out of the eye.

The amount of drug employed in the capsule will vary widely depending on the effective dosage of the drug (for example, the selected interferon required) and the rate of release from the microcapsule. Usually the drug will be from about 1 to 80, more usually 20 to 40 weight % of the microcapsule.

Other agents may be employed within the microcapsule for a variety of purposes. In addition to the drug agent, buffering agents and preservatives may be employed. The water soluble preservatives include sodium bisulfite, sodium thiosulfate, ascorbate, benzalkonium chloride, chlorobutanol, thimerosal, phenylmercuric borate, parabens, benzyl alcohol and phenylethanol. These agents may be present in amounts of from about 0.001 to 5% by weight and preferably about 0.01 to 2%. Suitable water soluble buffering agents are alkali or alkaline earth carbonates, phosphates, bicarbonates, citrates, borates, acetates, succinates and the like, such as sodium phosphate, citrate, borate, acetate, bicarbonate and carbonate. These agents may be present in amounts sufficient to maintain a pH of the system of between about 2 to 9 and preferably about 4 to 8. As such the buffering agent may be as much as 5% on a weight to weight basis of the total composition.

The particles may be of a narrow or broad range in size, normally not exceeding 300 μm, so as to be capable of being administered with a needle of appropriate size. Usually, the particle range will not differ by greater than about 200% of the average particle size, more usually not greater than about 100%. The average particle size will usually be in the range of about 0.5 μm to 2 mm, more usually in the range of about 10 μm to 1 mm. In some instances the particles will be selected to have an average diameter in the range of about 25–500 μm, to provide smaller depots. The size of the particle can be used to control the rate of release, period of treatment and drug concentration in the eye. In some situations mixtures of particles may be employed, employing the same or different pharmacological agent. In this way in a single administration a course of drag treatment may be achieved, where the pattern of release may be greatly varied.

Various techniques may be employed to produce the encapsulated drugs. Useful techniques include solvent-evaporation methods, phase separation methods, interfacial methods, spray-drying methods and the like.

In preparing the encapsulated drugs, for the most part solvent-evaporation methods will be employed. Towards this end, the preformed rate-controlling polymer is dissolved in a volatile, substantially water immiscible solvent, such as chloroform, methylene chloride, or benzene. Sometimes, the water immiscible solvent will be modified with a small amount of a water-miscible organic cosolvent, particularly an oxygenated solvent, such as acetone, methanol, ethanol, etc. Usually, the water-miscible organic cosolvent will be less than about 40 volume %, usually less than about 25 volume %. The drug may then be added to the polymer-solvent solution. Depending upon the nature of the drag, one may have the drug dispersed in the viscous polymer-solvent mixture or a solid dispersion of drug particles, where the drug will have been pulverized to obtain a fine powder, usually a microfine powder particularly of a size of less than about 1 mm, usually less than about 0.5 mm, preferably between about 1 to 3 μm and may be about 0.5 μm or smaller.

The amount of polymer employed in preparing the microcapsules will vary with the size of the particle desired, the use of additional coatings, the viscosity of the solution, the solubility of the polymer and the like. Usually, the concentration of polymer will be in the range of 10 to 80 weight %. The ratio of drug to polymer will vary with the desired rate of release, the amount of drug generally varying in the range of 1 to 80 weight % of the polymer.

The dispersion or solution obtained above is added to a rapidly stirred aqueous solution comprising water and a dispersing agent, which may be a protective colloid. Of particular interest as macromolecular dispersing agents are agents such as poly(vinyl alcohol) (1–10%) or non-ionic detergents, such as Span detergent.

The volume of the organic phase will be smaller than the aqueous phase, generally being in a volume ratio of from about 1:1 to $10^3$ of organic to aqueous phase. An oil-in-water emulsion is then produced by stirring. The rate of stirring is selected to produce the appropriate droplet size and stirring is continued throughout the next step.

The microencapsulation vessel containing the emulsion is then closed and a mild vacuum is applied to the system to evaporate the volatile organic solvent. The solvent should be evaporated slowly, since too rapid evaporation results in bubbles and blow holes formed in the microcapsule walls. The rate of evaporation may be determined empirically, using the experience reported in the literature. Usually the vacuum will be in the range of about 3 to 10 mm Hg. After evaporation has been completed, the resulting microcapsules are centrifuged, washed completely with water, collected, (e.g., collection by filtration), and drained. Usually, the microcapsules will then be subdivided with sieves to isolate particle of a size range of the desired diameter.

The process may be carded out conveniently at room temperature, but cooling or heating may be employed in specific situations to optimize the process. The ratio of drug to polymer is adjusted to produce optimized compositions, since the final product will normally result in the initial ratio. By manipulating the initial bulk viscosity of the drug-polymer-solvent mixture and of the aqueous dispersing medium, along with the stir rate, production of microcapsules with the desired size may be optimized. Moreover, the composition of dissolved organic solvent and the rate of solvent evaporation can be tested to produce microcapsules with larger or smaller crystals of drug in the microcapsules. For polymers which are hydrolytically sensitive, the microcapsules should not be exposed to the aqueous dispersing medium for excessively long periods during the solvent-evaporation step.

The particle size distribution of each batch of microcapsules will be relatively narrow. However, when desired, the size-fractions may be further refined by a physical separation process such as dry or wet sieving.

In order to define the potential drag-release behavior of the microcapsules in vivo, a weighed sample of microcapsules may be added to a measured volume of a solution containing four parts by weight of ethanol and six parts by weight of deionized water. The mixture is maintained at 37° C. and stirred slowly to maintain the microcapsules suspended. The appearance of the dissolved drag as a function of time may be followed spectrophotometrically until the absorbance becomes constant or until greater than 90% of the drug has been released. The drug concentration after 1 h in the solution is indicative of the amount of free unencapsulated drug in the dose, while the time required for 90% drug to be released is related to the expected duration of action of the dose in vivo. As a general rule, one day of drag release in vitro is approximately equal to 35 days of release in vivo. While release may not be uniform, normally the release will be free of larger fluctuations from some average value which allows for a relatively uniform release.

Intraocular administration, where the drug may be either encapsulated or unencapsulated, may be achieved in a variety of ways including injection, infusion, trocar, etc. Various techniques for introducing materials into the posterior segment of the eye are well known (see, for example, Liu, et al. (1987) *Ophthalmology* 94: 1155–1159 and references cited therein). When unencapsulated, the amount of interferon injected into the posterior segment will be from at least from about 10,000 to 640,000 units, normally from about 50,000 to 100,000 units, preferably about 75,000 units per treatment. Where microcapsules are employed, the amount of microcapsules injected will be sufficient to provide for maintenance of an effective concentration of the drug within the posterior segment, said concentration being equivalent to at least about 20,000 units, generally from at least about 10,000 to 640,000 units, normally from about 50,000 to 100,000 units, preferably about 75,000 units, and may be optimized. Where unencapsulated interferon is employed, the number of injections required will generally range from at least 1 to about 6, generally at least about 3 injections. Where unencapsulated interferon is employed, the drug will be administered at intervals ranging from about 3 to 42 days, usually between 7 to 36 days, preferably about 21 days between injections. Where microcapsules are employed, the number of injections required will be 3 or fewer, preferably 1. Depending upon the mode of delivery utilized (for example whether direct injection of the interferon or injection of microcapsules containing interferon is utilized), the amount of drag administered, the number of injections and patient tolerance, the length of the period between injections may vary and may be optimized.

The method of treatment of the subject invention may accompany laser photocoagulation treatment, which cauterizes leaking blood vessels of the established SRNM. The additional treatment of intraocular administration of drag may find use in the prevention of the recurrence of neovascularization that often follows conventional laser treatment. Such additional drag treatments may be administered substantially before, substantially concurrent with, or shortly after laser treatment.

The method of treatment of the subject invention may also find use as a prophylactic therapy. Intraocular administration of interferon may prevent occurrence of disease in susceptible patients or the development of AMD in the unaffected eye of patients with unilateral AMD. Such prophylactic treatment may be administered to AMD-susceptible patients when the patient reaches an approximate age at which the patient may be expected to soon succumb to disease, e.g. about 52 years. Prophylactic treatment of the unaffected eye of patients with unilateral AMD may begin substantially concurrent with, or substantially shortly after, diagnosis of AMD in the affected eye.

The following examples are offered by way of illustration and not by way of limitation.

EXPERIMENTAL

In one embodiment of the invention, a patient presenting with serous macular detachment and hemorrhage was treated with intraocular administration of α-2a interferon (Roferon-A, Hoffmann La-Roche). The history of the macular degenerative disease of this patient is presented in Table 1. This patient was subjected to laser photocoagulation therapy. However, laser therapy proved to be only partially successful and eventually subretinal neovascularization recurred. Following a second, unsuccessful laser treatment, the patient was treated according to the method of the subject invention. Specifically, 75,000 units of α-2a interferon in saline in a total volume of 100 µl were injected intravitreally with a 30 gauge needle. This treatment was repeated a second and third time, at 21 days and 42 days respectively, following the initial inoculation. Following the initial treatment with α-2a interferon, a dramatic decrease in the amount of hemorrhage was observed. A decrease in leakage from the blood vessels afforded better visibility of the subretinal neovascular membrane (SRNM). Following the second treatment, the hemorrhage and leakage were further decreased and some vessels of the SRNM were closed. One week after the third treatment, most of the abnormal, undesirable vessels of the SRNM were obliterated, with only a small amount of leakage remaining from a few vestigial vessels. Thus, intraocular administration of α-2a interferon was successful where laser treatment was unsuccessful. Furthermore, these successful results were achieved in only three treatments given over a time period of only 2 months.

feron contained within the microcapsules placed in the posterior segment of the eye neither migrates to the anterior chamber of the eye nor affects the other, untreated eye. Furthermore, the interferon continues to be released from the microcapsules for approximately 4 months. The necessity for subsequent treatments is determined by fluorescein angiographic examination at approximately 2 to 3 weeks following the initial treatment.

It is evident from the above results that intraocular administration of drugs can find effective use in the treatment of macular degeneration, particularly the wet form of the disease. Of especial interest is the use of interferon as the drug of choice, particularly α-2a interferon. Systemic

TABLE 1

Results of Intraocular Administration of α-2a Interferon

| Day* | Clinical Manifestation | Fluorescein Examination | Description | Treatment |
| --- | --- | --- | --- | --- |
| — | macular hemorrhage | hemorrhage; no SRNM** observed | small retinal hemorrhage in macula with no active serous leakage | observe |
| 320 | serous macular detachment; Occult SRNM | occult SRNM with leakage | drusen and pigment epithelial defects in macula; progressive leakage with serous macular detachment | laser treatment #1 |
| 334 | serous macular detachment | less leakage | "hot spot" present temporally indicating possible leakage site; treated area better; less leakage | observe |
| 374 | | SRNM persistence and recurrence | "hot spot" persists; SRNM increased in size and prominence with extension nasally and superiorly | laser treatment #2 |
| 458 | | | SRNM growth with more blood vessels branching out; SRNM extending inferior temporally; increased leakage | |
| 478 | serous and hemorrhagic macular detachment | increased leakage and hemorrhage | further growth and extension of SRNM temporally and superior nasally with new hemorrhage; increased leakage from SRNM; rapid leakage obscures details | interferon injection #1 |
| 499 | serous and hemorrhagic macular detachment | decreased leakage and hemorrhage | decreased hemorrhage temporally; less leakage; better visibility of SRNM | interferon injection #2 |
| 520 | serous and hemorrhagic macular detachment | decreased leakage | decreased hemorrhage and leakage; still better view of SRNM; some vessel closure in SRNM; no circulation | interferon injection #3 |
| 527 | serous and hemorrhagic macular detachment | decreased leakage | most vessels in SRNM obliterated; only small amount of leakage from a few vestigial vessels | observe |

Day* = indicates number of days post-presentation
SRNM** = subretinal neovascular membrane In a second embodiment of the invention, the drug of choice is contained within a biocompatible, biodegradable microcapsule. Preparation of such microcapsules is described in U.S. Pat. No. 4,853,224. In a preferred embodiment, microcapsules comprising α-2a interferon are employed. Such microcapsules are prepared by first solubilizing an appropriate weight of polymer, preferably a polyester of hydroxycarboxylic acid, with a water immiscible organic volatile solvent, e.g. benzene, methylene chloride or chloroform. The α-2a interferon is added to the mixture at an amount in the range of at least about 50:50 mixture by weigh of polymer:lyophilized α-2a interferon to form a slurry which is mixed to substantial homogeneity. The slurry is then added dropwise to a vessel containing rapidly stirred deionized distilled water in a volume ratio of 1: 0.5–1×103 (organic slurry:water). The water is 1–10 weight % polyvinyl alcohol. The vessel is sealed and a mild vacuum applied slowly to prevent bubbles and blow holes in the microcapsules over a period of about 8–10 hrs. After evaporation of the solvent, the microcapsules are centrifuged, washed repeatedly with sterile distilled water, filtered and drained. The microcapsules are sized with sieves and dried in vacuo. A volume of microcapsules sufficient to release 75,000 units of α-2a interferon over a period of 3 weeks are resuspended in a total volume of 100 μl saline and are directly introduced into the vitreous humor of the eye of the patient by injection with a 30 gauge needle. The interadministration requires greatly elevated levels of drug administration to the host in order to achieve an effective level in the eye. Because intraocular administration places the drug directly at the site, a significantly lower level of the drug is required. Thus intraocular administration, especially where microcapsules are employed, provides for very efficient use of the drug by concentrating and retaining the agent at the site where it is needed. The method of treatment of the subject invention provides advantage over subcutaneous administration in providing a more economical therapy and, in part as a result of the lower drug dosage requirement, in avoiding the side effects associated with systemic administration. Intraocular inoculation of the drug of choice also obviates the need to cross the blood-eye barrier in order to reach the macula. Where microcapsules are employed in intraocular administration to provide for slow release of the drug at the site of the disease, the frequency of administrations is significantly reduced. Thus, one or only a few administrations of the drug may be required for treatments over an extended period of time, reducing the burden on the patient, ensuring continued and controlled medication, and minimizing the interference with the activities of the patient.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of treatment of macular degeneration associated with subretinal neovascularization in a mammalian host, said method comprising the steps of:

administering intraocularly interferon to said host in an amount sufficient to elicit a decrease in hemorrhage or leakage associated with said subretinal neovascularization wherein said administering is by at least 3 injections at intervals from about three to 42 days.

2. The method according to claim 1, wherein said interferon is α-2a interferon.

3. The method according to claim 2, wherein said amount is from at least about 10,000 to 640,000 units.

4. The method according to claim 1, wherein said interferon is encapsulated in a biodegradable microcapsule for slow release of said interferon.

5. A method of treatment of macular degeneration associated with subretinal neovascularization in a human host, said method comprising the steps of:

injecting intraocularly at least three injections at intervals of from about three to forty-two days of α-2a interferon to said human host in an amount ranging from at least about 10,000 to 100,000 units, said amount being sufficient to elicit a decrease in hemorrhage or leakage associated with said subretinal neovascularization.

6. A method of treatment of macular degeneration associated with subretinal neovascularization in a human host, said method comprising the steps of:

administering intraocularly interferon contained within biodegradable microcapsules to said host in an amount sufficient to maintain an intraocular concentration over a period of from about two weeks to 14 months so as to elicit a decrease in hemorrhage or leakage associated with said subretinal neovascularization.

7. The method according to claim 6, wherein said interferon is α-2a interferon.

8. The method according to claim 7, wherein said intraocular concentration is from at least about 10,000 to 100,000 units.

9. The method according to claim 6, wherein said biodegradable microcapsules comprise a biocompatible polyester of a hydroxycarboxylic acid.

* * * * *

UNITED STATES PATENT AND TRADEMARK OFFICE
CERTIFICATE OF CORRECTION

PATENT NO. : 5,632,984

DATED : May 27, 1997

INVENTOR(S) : Wong et al.

It is certified that error appears in the above-indentified patent and that said Letters Patent is hereby corrected as shown below:

In the cover sheet insert the reference --Fung, "Interferon Alpha 2a for Treatment of Age-Related Macular Degeneration" *Am. J. of Ophthalmology*, 112(3):349-350 (1991)--, as included in our PTO form 1449 filed on September 1993.

Column 2, line 46; column 4, line 8; column 6, lines 32 and 50; column 7, lines 45, 51, 58; and column 8, lines 24 and 31 [drag] and should read --drug--

Signed and Sealed this

Twenty-seventh Day of January, 1998

*Attest:*

BRUCE LEHMAN

*Attesting Officer*  *Commissioner of Patents and Trademarks*